United States Patent [19]
Rozencwaig

[11] Patent Number: 4,661,966

[45] Date of Patent: Apr. 28, 1987

[54] METHOD OF MEDICAL TREATMENT WITH SEROTONIN ANTAGONISTS

[76] Inventor: Roman Rozencwaig, 4721 The Boulevard, Westmount, Quebec, Canada

[21] Appl. No.: 770,440

[22] Filed: Aug. 29, 1985

[51] Int. Cl.⁴ .......................................... A61K 31/445
[52] U.S. Cl. .................................. 514/325; 514/319
[58] Field of Search ............................. 514/319, 325

[56] References Cited

U.S. PATENT DOCUMENTS 4,444,778  4/1984  Coughlin .......................... 514/324

OTHER PUBLICATIONS

Chemical Abstracts 97:409t (1982).
Chemical Abstracts 100:203268z (1984).

*Primary Examiner*—Jerome D. Goldberg
*Attorney, Agent, or Firm*—Schwartz, Jeffery, Schwaab, Mack, Blumenthal & Evans

[57] ABSTRACT

Treatment of patients suffering from acquired immuno deficiency syndrome, multiple sclerosis, Alzheimer's disease, by administration of a serotonin antagonist, said administration taking place once a day during the evening.

4 Claims, No Drawings

METHOD OF MEDICAL TREATMENT WITH SEROTONIN ANTAGONISTS

BACKGROUND OF INVENTION

1. Field of the Invention

This invention relates to a method of treatment of conditions such as acquired immuno deficiency syndrome, multiple sclerosis and Alzheimer's disease, and other conditions associated with old age, by serotonin antagonists and primarily cyproheptadine.

2. Description of Prior Art

There is a considerable number of studies on the ageing process, including the factors and agents responsible, and there are some suggestions to alleviate it. Some of the diseases often associated with old age include Alzheimer's disease, various heart diseases, arthritis, etc. In two articles which have appeared in 1982—P.S. Timiras et al, The Ageing Brain: Cellular and Molecular Mechanisms of Ageing in the Nervous system, edited by E. Giacobini et al., Raven Press, New York—Developing and Ageing Brain Serotonin Systems; and P.S.T. Timiras et al, Age and Aging (1982) 11, 73–88—there are discussions on the effect of serotonin on the ageing process. These studies have shown that serotonin accumulates in the central nervous system, with increasing age in a linear fashion, whereas its metabolite, melatonin, produced in the pineal gland decreases during aging.

The chemical cyproheptadine is a known serotonin antagonist and although other serotonin antagonists are known, the present discussion will be restricted to cyproheptadine because it is most available at present with least side effects. Numerous references describe the various medical uses of cyproheptadine. The following list is only partial:

(1) Studies of Mechanism of Cyproheptadine-induced Weight Gain in Human Subjects, John N. Stiel et al., *Metabolism*, March, 1970, 19 (3) pp?

(2) Experimental Study on Atherosclerosis, an Attempt at its Prevention and Treatment, Acta Pathol. Jap. Feb. 1969, 19(1) pp. 15–43.

(3) A Preliminary Report on BC-105: a new Antidepressant, Psychosomatics, Jan.-Feb. 1969, 10(1) pp.51-2.

(4) More on Cyproheptadine in Cushing's Disease, New England J. Med. 10 March 1977, 296 (10) pp. 576-7.

It is worthwhile considering the potential therapeutic use of cyproheptadine. Cyproheptadine has been investigated as a way of overcoming anorexic effects by stimulating appetite.

The ageing process is characterized by a group of progressive diseases such as arteriosclerotic heart disease, cardiovascular accidents, hypertension, arthritis, diabetes, Alzheimer's disease and an increase in age-related cancers. The serotonergic neurotransmitter system which is dominant in the central nervous system, and which directly effects the entire neuroendocrine system via the hypothalamic petuitary axis, is proposed in the prior art to be responsible for the ageing process for the following reasons.

By referring to the tables in the references of the Timiras et al mentioned above, it can be seen that serotonin promotes cystogenesis and causes general chronic inflammatory fibrotic changes, gradually leading to a replacement of normal tissues by chronic inflammatory debris-forming séars which in turn lead to increases in rigidity, decreased transport of nutrients and subsequent organ failure.

It is therefore believed that by administering an agent which is a serotonin-antagonist and which can cross the blood brain barrier to act within the central nervous system, this serotonin-antagonist would then act in effect as an anti-ageing substance and in that respect may also be used in the treatment of diseases of the aged, and other acute diseases.

SUMMARY OF INVENTION

It is an object of the present invention to provide a method of treatment of conditions such as Alzheimer's disease, acquired immuno deficiency syndrome and multiple sclerosis, and other conditions associated with old age by administering a serotonin antagonist in such a way to treat or at least alleviate such diseases.

It is another object of the present invention to provide a method for the treatment of patients suffering from acquired immuno deficiency syndrome, Alzheimer's disease, and multiple sclerosis, which comprises administering a serotonin antagonist to the patients, this administration essentially taking place once a day every evening.

In accordance with a preferred embodiment of the invention, the administration takes place between about 6 and about 10 o'clock p.m.

In accordance with another preferred embodiment of the invention, the administration takes place with doses of about 0.5 to 4 mg. of serotonin antagonist.

Preferably, the serotonin antagonist is conditioned in a suspension or in a tablet. The preferred serotonin antagonist obviously comprises cyproheptadine, because it is readily available.

Result of Test Treatments

The method of treatment according to the invention consists of the administration of cyproheptadine in a dose from 0.5 to 4 mg. orally either by a tablet or in liquid suspension. The administration took place every evening between 6 to 10 p.m., depending on the season, earlier in winter and later in the summer.

Patients E, F, G suffering from Alzheimer's disease.

These patients were treated with a dose from 2 to 4 mg. of cyproheptadine every evening. Four months after initiating the treatment, a test for recent memory has shown that there was an improvement by 50% and the general condition of the patient improved subjectively in all three cases. There was no further deterioration in any of the cases.

Explanations

As mentioned above it was suspected that a serotonin antagonist would be useful in the treatment of the diseases of the aged. However, the prior art is mute with regard to the successful treatment of Alzheimer's disease. It is believed that the treatment according to the invention is successful in view of the following.

It is suggested that cyproheptadine acts not merely as a serotonin antagonist but at the same time it is a melatonin agonist. We propose that it is the relative increase of serotonin over melatonin as well as the absolute decrease of melatonin that is of significance at least to the posology indicated above. Thus, it is suggested that cyproheptadine acts as a serotonin antaqonist and as well as a melatonin agonist. In this respect, this is the reason why it has to be given in the evening, since this is when the action of melatonin takes place. This action of cyproheptadine when administered in the evening is new and has not previously been described, at least to my knowledge. In other words, the dual function of melatonin agonist and serotonin antagonist of cyproheptadine has not been shown in the prior art.

The prior art has shown that when given during the day, the serotonin antagonist may actually be harmful. However, in view of the dual properties of the serotonin antagonist, when administered at night, the effect is beneficial.

Of course, it is within the scope of the present invention to use other serotonin antagonists in addition to cyproheptadine. This disclosure was restricted to that particular compound because it was more readily available. The present treatment is also applicable to other acute diseases such as acquired immuno deficiency syndrome, and multiple sclerosis.

I claim:

1. A method for the treatment of patients suffering from Alzheimer's disease, which comprises orally administering doses of about 0.5 to about 4 milligrams of cyproheptadine to said patients, said administration essentially taking place once a day every evening.

2. A method according to claim 1, wherein said administration takes place between about 6 and about 10 o'clock p.m.

3. A method according to claim 2, wherein said cyproheptadine is conditioned in a suspension.

4. A method according to claim 2, wherein said cyproheptadine is conditioned in a tablet.

* * * * *